United States Patent [19]
Gidda et al.

[11] Patent Number: 4,829,073
[45] Date of Patent: May 9, 1989

[54] THIADIAZOLE OXIDES FOR TREATING GASTROINTESTINAL MOTILITY DISORDERS

[75] Inventors: Jaswant S. Gidda, Carmel, Ind.; Ivo Monkovic, Durham, Conn.

[73] Assignee: Bristol-Myers Company, New York, N.Y.

[21] Appl. No.: 193,025

[22] Filed: May 12, 1988

[51] Int. Cl.⁴ .......................................... A61K 31/445
[52] U.S. Cl. .................................................. 514/326
[58] Field of Search ........................................ 514/326

[56] References Cited

U.S. PATENT DOCUMENTS 4,394,508  7/1983  Crenshaw et al. .................. 540/480

Primary Examiner—Frederick E. Waddell
Attorney, Agent, or Firm—Aldo A. Algieri

[57] ABSTRACT

The present invention provides a method for treating gastrointestinal motility disorders and thiadiazole oxide compounds for use in the method.

5 Claims, No Drawings

THIADIAZOLE OXIDES FOR TREATING GASTROINTESTINAL MOTILITY DISORDERS

BACKGROUND OF THE INVENTION

1. Field of the Invention

The present invention relates to a method for treating gastrointestinal motility disorders and compounds for use in the method and in particular a method for treating disorders associated with delayed gastric emptying and upper bowel transit.

2. Disclosure Statement

Impaired motility of the alimentary canal can lead to a variety of gastrointestinal diseases and symptoms such as gastroesophageal reflux, reflux esophagitis, diffuse esophageal spasms, gastric stasis, intestinal obstruction, paralytic ileus, abdominal pain, nausea, vomiting and constipation. Disorders associated with delayed gastric emptying can be caused by mechanical obstruction due to increased resistance or functional obstruction due to pump failure.

Functional gastric obstruction may be produced, for example, by certain drugs such as anticholinergics, narcotics and calcium channel blockers; metabolic disorders such as diabetic neuropathy and hypothyroidism; electrolyte imbalance including hypokalemia, hypocalcemia or hypomagnesemia; central or peripheral neurological disorders; inflammation of the stomach due to infective agents or vasculitis; abdominal trauma; severe pain; caloric deprivation such as anorexia nervosa; gastric ulcer; and tachygastria (ectopic gastric pacemaker).

Treatment of these diseases may be undertaken with a variety of motility enhancing (gastroprokinetic) agents such as muscarinic agonists, cholinesterase inhibitors, metoclopramide and domperidone. Available therapy is limited, however, by lack of specificity, potency, and/or side effects. The clinically preferred method of treatment in man is with metoclopramide hydrochloride (Reglan ®) as indicated in Physicians' Desk Reference, pages 1634–1636 (1987). However, metoclopramide has been shown to have both cholinergic and dopamine antagonistic effects. And because metoclopramide crosses the blood-brain barrier it may be associated with side-effects such as sedation and extrapyramidal changes in a large percentage of patients and at higher doses a number of other side-effects have been observed. Hence, there is a need for an agent which will enhance gastrointestinal motility and be devoid of side effects.

Recent reviews on the development of gastrointestinal motility enhancing agents and motility disturbances may be found in J. S. Gidda and I. Monkovic, *Annual Reports in Medicinal Chemistry*, 20, 117–125 (1985), in R. S. Fisher, *Scandinavian J. Gastroenterology*, 20 (suppl. 109), 59–68 (1985), and in references cited therein.

There is described in U.S. Pat. No. 4,394,508 issued July 19, 1983 to R. R. Crenshaw and A. A. Algieri a series of thiadiazole oxide compounds which are histamine $H_2$-receptor antagonists and inhibit gastric acid secretion and, therefore, are useful in the treatment of peptic ulcers. There is no disclosure that any of these compounds have motility enhancing properties or use as gastroprokinetic agents. In addition, the three commercially available histamine $H_2$-receptor antagonists, cimetidine (Tagamet ®), ranitidine (Zantac ®) and famotidine (Pepcid ®) are not indicated as gastroprokinetic agents [Physicians' Desk Reference, pages 2031–2033 (1988), pages 1028–1029 (1988) and pages 1380–1381 (1988), respectively].

Surprisingly, we have found that certain compounds disclosed in U.S. Pat. No. 4,394,508 are effective gastric motility enhancing agents which may lack the potential side effects associated with the present agents, and therefore, are useful in the treatment of gastrointestinal motility disorders.

SUMMARY OF THE INVENTION

The present invention relates to a method for treating a patient suffering from a motility disorder of the gastrointestinal tract such as delayed gastric emptying and gastroesophageal reflux, by administering to said patient a therapeutic amount of a compound of the formula

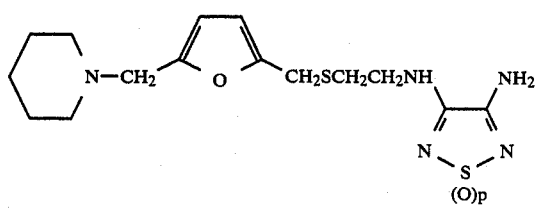

wherein p is 1 or 2 or a non-toxic pharmaceutically acceptable salt thereof.

DESCRIPTION OF THE INVENTION

The present invention provides a method of treating a patient suffering from a gastromotility disorder, for example, delayed gastric emptying or gastroesophageal reflux by administering to said patient a therapeutically effective amount of a compound of the formula

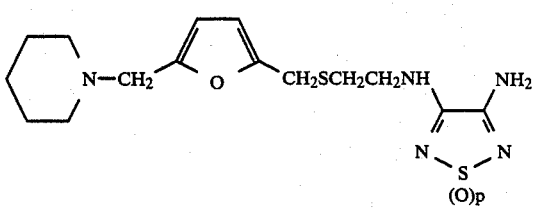

I wherein p is 1 or 2 or a non-toxic pharmaceutically acceptable salt thereof.

In particular, the compounds of Formula I are useful in the treatment of a variety of disorders associated with impaired motility of the alimentary canal. These motility disorders are associated with gastrointestinal diseases and symptoms such as gastroesophageal reflux, reflux esophagitis, diffuse esophageal spasms, gastric stasis, intestinal obstruction, paralytic ileus, abdominal pain, nausea, vomiting, constipation, intubation and disorders associated with delayed gastric emptying caused by functional obstruction due to pump failure. Functional gastric obstruction may be produced, for example, by certain drugs such as anticholinergics, narcotics and calcium channel blockers; metabolic disorders such as diabetic neuropathy and hypothyroidism; electrolyte imbalance including hypokalemia, hypocalcemia or hypomagnesemia; central or peripheral neurological disorders; inflammation of the stomach due to infective agents or vasculitis; abdominal trauma; severe pain; caloric deprivation such as anorexia nervosa; gastric ulcer; and tachygastria (ectopic gastric pacemaker).

Preferably, the compounds of Formula I are useful as motility enhancing (gastroprokinetic) agents in the treatment of motility disorders associated with delayed gastric emptying such as gastroesophageal reflux, gastric stasis and functional gastric obstruction. More preferably the gastroprokinetic agent is the compound of Formula I wherein p is 1.

The compounds of Formula I wherein p is 1 or 2 are prepared by the procedures described in U.S. Pat. No. 4,394,508. The compound of Formula I wherein p is 1 is preferred.

Usefulness of the compounds of Formula I in therapeutic methods of the present invention is demonstrated by the results from both in vitro and in vivo gastroprokinetic pharmacological procedures.

In Vitro Gastroprokinetic Activity

Two classical pharmacological preparations, the field stimulated guinea pig ileum and field stimulated rat fundic strip, are utilized to assess gastroprokinetic activity in vitro.

1. Electrically Stimulated Isolated Guinea Pig Ileum

A modification of the procedure described by W. D. M. Paton, *J. Physiol.* (Lond), 127, 40-41P (1955). Segments of the preterminal ileal tissue, 3-4 cm in length, are mounted in a 20 ml tissue bath. The tissues are perfused at 37° C. with a modified Krebs solution and continuously gassed with 95%$O_2$-5% $CO_2$. The solution is prepared with millipore water and consists of (mM/L): NaCl 116, KCl 5, $CaCl_2$ 2.5, $KH_2PO_4$ 1.2, $MgSO_4.7H_2O$ 0.5, $NaHCO_3$ 25 and Glucose 11.1.

A force displacement transducer is attached to each tissue and the resting tension adjusted to 1.0 g. The tissues are allowed to equilibrate for one hour, with washes every twenty minutes, after the stimulator is engaged or until twitch height remains stable. The contractions of the longitudinal muscle of the ileum are recorded by means of the force displacement transducer and are displayed on a Beckman RP dynograph.

Dose response curves for test compounds are established by adding single doses of the material in increasing increments until a maximal effect is achieved. Compounds are administered at volumes ranging from 0.2 to 0.6 ml to give final bath concentrations of 0.1 $\mu$M thru 100 $\mu$M. The test materials remain in contact with the tissue for 2 to 3 minutes, until the peak effect is achieved, before thorough washing with Kreb's solution. When the tissues return to predose contractile amplitude, an increased concentration of drug is given.

For the compound of Example 1 there was obtained a computer projected EC50 value of 224 $\mu$M with 95% confidence limits of 84–1629 and an increase in contractile amplitude with a maximal response of 37±4.8% over control.

2. Electrically Stimulated Isolated Rat Stomach Fundus

The rat fundic strip is prepared according to the method described by J. R. Vane, *Brit. J. Pharmacol.*, 12, 344–349 (1957). For this preparation, strips are made by removing the fundal end of the stomach and slitting it open to form a sheet. Small cuts are made transversing the longitudinal muscle to produce two strips 3-4 cm in length. The tissues are mounted in a 20 ml organ bath containing Kreb's solution at 37° C. and are oxygenated with 95% $O_2$-5% $CO_2$. Resting tension is adjusted to 1.0 g. Contractions are recorded by means of a force displacement transducer and a Beckman Dynograph Type R.

Once a consistent response to electrical field stimulation is established, varying amounts of a test compound are added to the bath. All compounds are administered three minutes prior to electrical stimulation at volumes of 0.2 ml to 0.6 ml for final bath concentrations of 0.1 $\mu$M thru 100 $\mu$M. Each tissue is thoroughly washed between each dose. A dose response curve is achieved by measuring the effect of increasing dose levels of test materials on the tissue contraction due to electrical field stimulation.

For the compound of Example 1, there was obtained an EC50 value with 95% confidence limits of 8.2 (5.7–13) $\mu$M and an increase in contractile force with a maximal response of 82±10% over control.

Enhancement of the electrically-induced smooth muscle contractions is the criteria for prokinetic activity and the compound of Example 1 was efficacious in both in vitro models.

IN VIVO SMALL ANIMAL GASTROPROKINETIC ACTIVITY

The method used to assess rat emptying is a modification of the procedures described by D. A. Droppleman et al., *Journal of Pharmacological Methods*, 4, 227–230 (1980). Test compunds (0.3 to 30 mg/kg in 1 ml/kg vehicle) are administered either orally or subcutaneously to male, Sprague-Dawley rats (160-180 g) that were fasted overnight. The test animals receive 2.5 ml of a freshly made milk plus ground rat chow meal by oral intubation, thirty or fifteen minutes following oral or subcutaneous administratioin, respectively. Rats are sacrificed 25 minutes following the test meal, and the stomachs are quickly excised. Each stomach containing the remaining meal is weighed intact on an analytical balance. To empty the contents before reweighing, each stomach is cut open, rinsed thoroughly and then blotted dry. The difference in weights indicates the amount of meal remaining in the stomach. The amount of meal retained is calculated as a percent of the total meal weight administered.

The compound of Example 1 was found to enhance stomach emptying in normal rats with a subcutaneous ED50 value of 0.40 (0.13–0.78) mg/kg and a maximum response of 105±6% over control values and an oral ED50 value of 2.9 (1.4–11) mg/kg having a maximum response of 95±19% over control values. Thus, the compound of Example 1 is potent and efficacious as a gastroprokinetic agent when given orally or subcutaneously to rats.

IN VIVO LARGE ANIMAL GASTROPROKINETIC ACTIVITY

1. Lower Esophageal Sphincter Pressure in the Anesthetized Opossum

This procedure measures the effect of the test compounds on the opossum lower esophageal sphincter (LES) which closely resembles the human sphincter. In order to test the effects of compounds on LES resting pressure, a small tube perfused with water at a constant flow rate is passed through the anesthetized opossum esophagus and water pressure in the tube is monitored. The method is similar to that described by R. Goyal et al., *Gastroenterology*, 71, 62–67 (1976).

An increase in esophageal tone is measured as an increase in pressure and reported as a percent increase of the control determination. The compound of Example 1 was given as a single bolus dose of 10 mg/kg I.V. in four opossums. At this dose it increased LES pressures by 33%, but at higher doses no inhibition of LES pressure following the initial increase was observed.

2. Gastric Contractile Activity in the Anesthetized Dog

The effect of test compounds on circular smooth muscle contractile activity of the antral and duodenal portion of the stomach are measured by strain gauge arches sewn on the serosal surface similar to the procedure described by A. W. Mangel et al., Digestion, 28, 205-209 (1983).

Male Beagle Dogs, weighing 8 to 14 kg, are fasted overnight and then anesthetized with pentothal (thiopental sodium), 20 mg/kg and maintained with I.V. alpha-chloralose (100 mg/ml in PEG 400, diluted 1:1 with saline immediately before use) as needed, usually 100 mg/dose. The trachea is intubated for respiratory assistance if needed, and the right femoral artery and vein are cannulated to monitor blood pressure and administer I.V. solutions, respectively.

The stomach and intestine are exposed by a midline incision, and a Walton-Brodie adjustable strain gauge arch is sewn on the ventral surface of the antrum of the stomach, 3-5 cm proximal to the pylorus. The arch is oriented to respond to contractions of the circular muscle, and the initial resting tension is set at 25 grams by adjusting the length of the arch.

The preparation is allowed to stabilize for 1 to 2 hours. Fifteen minutes after observation of migrating motor complex phase III activity, test compounds are given every 10 minutes in a cumulative dosing manner beginning at 0.01 mg/kg to 10 mg/kg. The test compounds are dissolved in saline at concentrations that are dependent on the weight of each animal so that a constant volume will be administered at each dose level. The cumulative doses evaluated are 0.01, 0.03, 0.1, 0.3, 1.0, 3.0 and 10 mg/kg for each test compound, while the corresponding volumes of saline plus test compound are 1.0, 2.0, 0.7, 2.0, 0.7, 2.0 and 0.7 ml, respectively. The stomach contractions, the cumulative grams of tension developed by the stomach contractions, EKG, heart rate, blood pressure, and any additional contractile and/or electrical activities are recorded on a Beckman Dynograph.

The results are expressed as the increased tension developed by the smooth muscles in response to the administration of test compound. Because the mean maximal response was approximately 20 grams, ED50 values were calculated as the dose necessary to achieve 50% of that value i.e., 10 grams. In this preparation, the compound of Example 1 increased the tension dose dependently with an ED50 value of 0.24 (0.09-0.62) mg/kg and a maximal response of developed tension of $24\pm5$ grams. In addition, the compound of Example 1 also increased the duodenal tension dose dependently.

3. Gastric Emptying of Solid Meal in Conscious Dogs

Under aseptic conditions 10 beagle dogs were implanted with T-shaped titanium duodenal cannulas. The dogs were allowed to recover from surgery for 3 weeks. Each dog before the test was fasted for 16-18 hours. Water was provided ad lib. On the day of the test, the duodenal cannula was opened and the stomach contents were drained. The cannula was closed again and the dog was dosed orally with either placebo (10cc saline) or with test compound in 10cc saline. After 30 minutes the dog was offered 200 grams of Alpo food. The dry weight of this food is 36 grams. After the dog had ingested the food the cannula was opened and an insert was placed in the cannula which drained the chyme through the cannula into a beaker. This collection was continued for 5 hours and samples were collected every thirty minutes. The chyme was filtered and dried in an oven. The dry weight collected every thirty minutes was deducted from the dry weight of the food left in the stomach. A time response curve of gastric emptying was developed and $t_\frac{1}{2}$, the time taken to empty 50% of the solid meal from the stomach was determined. The $t_\frac{1}{2}$ for the test compound at various doses was compared with controls. Significance of differences was determined using paired t-test.

TABLE I

Effect of metoclopramide, Ranitidine and compounds of Examples 1 and 2 on the gastric half emptying time ($T_\frac{1}{2}$) of a solid meal in conscious dogs.

| Dose** (mg/kg, P.O.) | $T_\frac{1}{2}$ (min) | | | |
|---|---|---|---|---|
| | Metoclopramid | Ranitidine | Compound of Ex. 1 | Compound of Ex. 2 |
| Control (N = 6 dogs) | 208 ± 34 | 208 ± 34 | 208 ± 34 | 208 ± 34 |
| 0.1 (N = 3) | 120 ± 21* | Not tested | 204 ± 32 | Not tested |
| 1.0 (N = 3) | 198 ± 14 | 206 ± 31 | 96 ± 14* | 110 ± 18* |
| 3.0 (N = 3) | Not tested | 206 ± 24 | 98 ± 16* | Not tested |

*Significantly different from control (P < .05)
**Metoclopramide was given 30 min before meal. Ranitidine and compounds of Examples 1 and 2 were given 60 minutes before meal.

The results in Table I show that orally at a dose of 1.0 mg/kg the compounds of Examples 1 and 2 significantly decreased the half emptying time ($t_\frac{1}{2}$) of a solid meal in conscious dogs while ranitidine was found to be ineffective at the tested doses. Thus, the compounds of the present invention are useful as gastroprokinetic agents when given orally to conscious mammals.

The results from the above biological tests show that the compounds of the present invention are useful in the treatment of gastrointestinal motility disorders, and in particular, delayed gastric emptying and gastroesophageal reflux disease. Radioligand binding studies to membrane receptors were carried out to assess the potential for interaction with other receptors. Our studies showed that the compound of Example 1 does not bind to any of the dopamine, serotonin, benzodiazepine, GABA or calcium channel receptors. To assess any possible cardiovascular effects a bolus injection of the test compound at various doses was administered to anesthetized dogs. Thus, the compound of Example 1, at 5 mg/kg administered I.V., had no effect on heart rate or blood pressure in three anesthetized dogs.

For therapeutic use, the pharmacologically active compounds of the present invention will normally be administered as a pharmaceutical composition comprising as the (or an) essential active ingredient at least one such compound in association with a solid or liquid pharmaceutically acceptable carrier and, optionally, with pharmaceutically acceptable adjuvants and excipients employing standard and conventional techniques.

The pharmaceutical compositions may be administered orally, parenterally or by rectal suppository. A wide variety of pharmaceutical forms may be employed. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. The pharmaceutical compositions are prepared by conventional techniques appropriate to the desired preparation containing appropriate amounts of the active component, that is, the compound according to the present invention.

The dosage of the compounds of the present invention will depend not only on such factors as the weight of the patient and mode of administration, but also on the severity of the gastromotility disorder and the potency of the particular compound being utilized. The decision as to the particular dosage to be employed (and the number of times to be administered per day) is within the discretion of the physician, and may be varied by titration of the dosage to the particular circumstances of this invention for the satisfactory treatment of the gastromotility disorder, each oral dosage unit will contain the active ingredient in an amount of from about 0.1 mg/kg to about 10 mg/kg body weight, and most preferably from about 0.5 mg/kg to about 5 mg/kg body weight. The active ingredient will preferably be administered in equal doses from one to four times a day. However, usually a small dosage is administered, and the dosage is gradually increased until the optimal dosage for the patient under treatment is determined.

EXAMPLE 1

3-Amino-4-{2-[(5-piperidinomethyl-2-furyl)methylthio]ethylamino}-1,2,5-thiadiazole 1-oxide The title compound was prepared according to the procedure described in U.S. Pat. No. 4,394,508.

EXAMPLE 2

3-Amino-4-{2-[5-piperdinomethyl-2-furyl)methylthio]ethylamino}-1,2,5-thiadiazole 1,1-dioxide To a stirred and cooled (ice-bath) suspension of 3,4-dimethoxy-1,2,5-thiadiazole 1,1-dioxide (890 mg, 5 mmol) in methanol (60 ml) was added dropwise a solution of 2-[(5-piperidinomethyl-2-furyl)methylthio]ethylamine (1.275 g, 5 mmol) in methanol (10 ml) following the procedure described in U.S. Pat. No. 4,394,508. After 5 hours, ammonia gas was bubbled into the mixture with cooling, and stirring was continued for 2 hours. The mixture was concentrated in vacuo, and the residue chromotographed on deactivated silica gel using a dichloromethane, methanol, ammonium hydroxide (100:6:0.5) solvent system to give 0.75 g of the title compound as a white amorphous solid.

Anal. Calcd. for $C_{15}H_{23}N_5O_3S_2$: C 46.75; H, 6.01; N, 18.17; S, 16.64. Found: C, 45.98; H, 6.05; N, 16.82; S, 14.90.

What is claimed is:

1. A method of treating a patient suffering from a motility disorder of the gastrointestinal tract which comprises administering to said patient a therapeutically effective amount of a compound of the formula

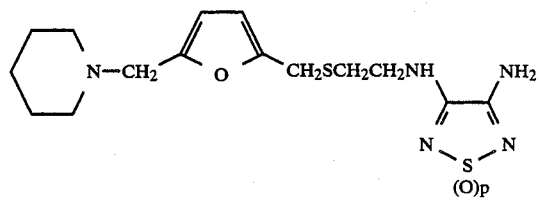

wherein p is 1 or 2 or a non-toxic pharmaceutically acceptable salt thereof.

2. A method according to claim 1 wherein said compound is 3-amino-4-{2-[(5-piperidinomethyl-2-furyl)methylthio]ethylamino}-1,2,5-thiadiazole 1-oxide.

3. A method according to claim 1 wherein said motility disorder is delayed gastric emptying.

4. A method according to claim 1 wherein said motility disorder is gastroesophageal reflux.

5. A method according to claim 1 wherein said motility disorder is gastric stasis.

* * * * *